(12) United States Patent
Meyer et al.

(10) Patent No.: US 8,354,028 B2
(45) Date of Patent: Jan. 15, 2013

(54) METHOD FOR SEPARATING AN ORGANIC PHASE FROM AN ELECTROLYTE-CONTAINING AQUEOUS AND ORGANIC PHASE

(75) Inventors: Helmut Meyer, Odenthal (DE); Guido Naberfeld, Upper St. Clair, PA (US); Johann Rechner, Kempen (DE); Rafael Warsitz, Essen (DE); Michael Traving, Burscheid (DE); Werner Bäcker, Wipperfürth (DE); Thomas Elsner, Düsseldorf (DE); Arno Nennemann, Bergisch Gladbach (DE); Stephan Bahnmuler, Signapur (DE); Gerhard Langstein, Kuerten (DE); Julia Hitzbleck, Köln (DE); Patrick Theato, Mainz (DE); Daniel Kessler, Weitersburg (DE); Daniel-Gordon Duff, Leverkusen (DE); Sascha Plug, Leverkusen (DE)

(73) Assignee: Bayer Material Science AG, Leverkusen (DE)

( * ) Notice: Subject to any disclaimer, the term of this patent is extended or adjusted under 35 U.S.C. 154(b) by 933 days.

(21) Appl. No.: 11/876,094

(22) Filed: Oct. 22, 2007

(65) Prior Publication Data

US 2008/0185343 A1  Aug. 7, 2008

(30) Foreign Application Priority Data

Oct. 25, 2006  (DE) .......................... 10 2006 050 381

(51) Int. Cl.
*B01D 11/00* (2006.01)
*B01D 24/00* (2006.01)

(52) U.S. Cl. .... 210/634; 210/799; 210/506; 210/500.21
(58) Field of Classification Search .................. 210/634, 210/799
See application file for complete search history.

(56) References Cited

U.S. PATENT DOCUMENTS

| | | | | |
|---|---|---|---|---|
| 4,318,785 A * | 3/1982 | Gunjima et al. | ................ | 156/60 |
| 5,051,182 A | 9/1991 | Wang | | |
| 5,268,150 A * | 12/1993 | Burkitt | .......................... | 422/102 |
| 6,541,272 B1 * | 4/2003 | Mitra | ............................ | 436/178 |
| 2004/0168981 A1 * | 9/2004 | Dudziak et al. | ............... | 210/644 |
| 2004/0211319 A1 * | 10/2004 | Kang et al. | ......................... | 96/11 |
| 2006/0076299 A1 * | 4/2006 | Feng et al. | ..................... | 210/748 |
| 2006/0237361 A1 | 10/2006 | Dudziak et al. | | |

FOREIGN PATENT DOCUMENTS

| | | |
|---|---|---|
| CA | 747994 | 12/1966 |
| DE | 4343754 | 7/1994 |
| DE | 19 510 061 A1 | 9/1996 |
| DE | 19510061 | 9/1996 |
| DE | 10 308 110 A1 | 9/2004 |
| EP | 0014462 | 8/1980 |
| EP | 0 038 986 A2 | 11/1981 |
| EP | 264 885 A2 | 4/1988 |
| JP | 52096697 | 8/1977 |
| JP | 52098090 | 8/1977 |
| WO | 0009582 | 2/2000 |

* cited by examiner

*Primary Examiner* — Krishnan S Menon
*Assistant Examiner* — Allison M Gionta
(74) *Attorney, Agent, or Firm* — Norris McLaughlin & Marcus PA

(57) ABSTRACT

A method for separating electrolyte-containing water from an organic phase by means of permeation on a hydrophobic separating means. The permeated organic solution is substantially depleted in water and the retained water is enriched with electrolytes.

3 Claims, 1 Drawing Sheet

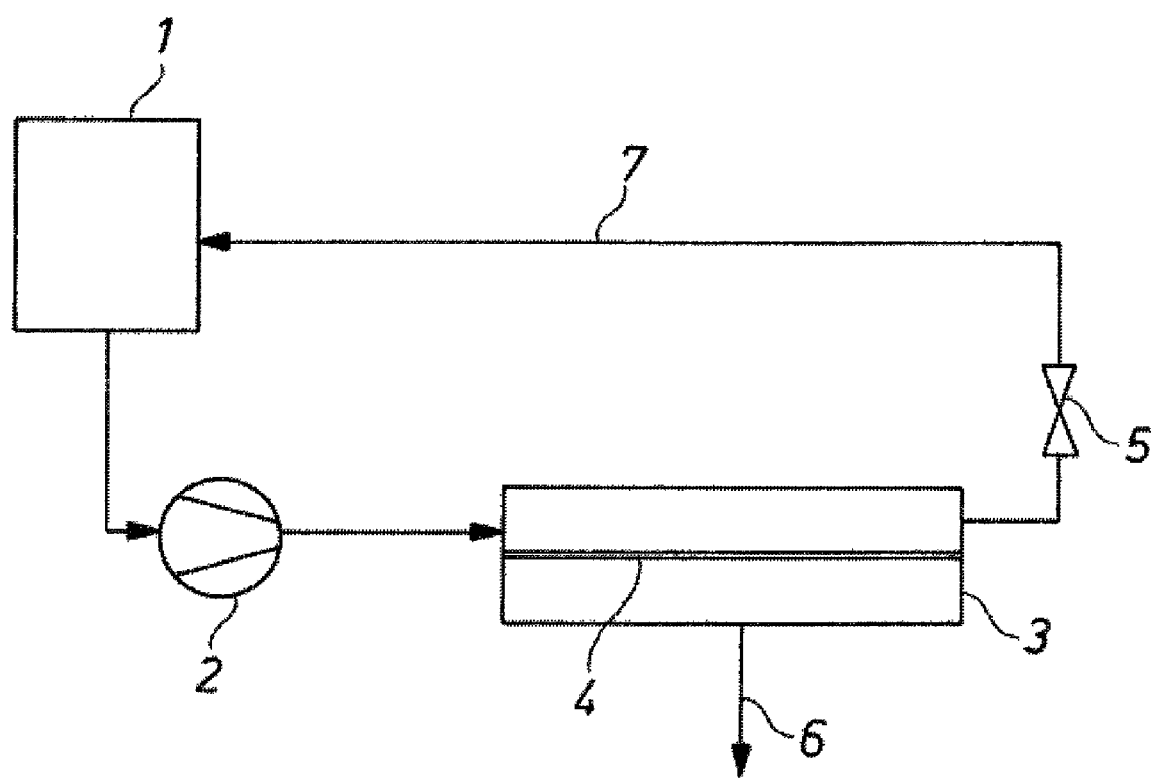

METHOD FOR SEPARATING AN ORGANIC PHASE FROM AN ELECTROLYTE-CONTAINING AQUEOUS AND ORGANIC PHASE

The invention relates to a novel method for separating an electrolyte-free organic phase from a mixture of electrolyte-containing (salt-containing) aqueous and organic phases. The electrolyte-containing water is dispersed or emulsified in the organic phase.

BACKGROUND OF THE INVENTION

The separation of electrolytes (salts, alkalis, acids) and water from organic phases, for example water-immiscible polymers, aromatics, aliphatics, plays an important role in industrial processes. According to the prior art, such separation has been carried out by means of centrifuging, deposition, distillation, spray drying, evaporation-extrusion, precipitation and/or fiber coalescence. In general, the separation of the electrolytes (alkali and acid) is not carried out until after neutralization to form the corresponding salts, with acids and alkalis.

A disadvantage is the consumption of neutralizing agents and the concomitant loss of alkali and/or acid, as well as disposal/use of the salt. Other disadvantages of the methods described above for separating an electrolyte-free (alkali, acid, salt) organic phase are that they necessitate on the one hand extensive use of energy in order to separate the water and, on the other hand, elaborate separation of residual contents of electrolytes (salts) by washing processes. This entails high costs owing to the associated water treatment and the high energy demand. Tests to improve the phase separation, for example temperature variation, improved centrifuges or reducing the size of the separators by using coalescence aids, often lead to insufficient separation or a strong susceptibility to clogging of the coalescence aids by build-up of salt.

In the specific case of the polyether polyol production process, the salts and residual water contents are separated from the polyol phase according to the prior art by centrifuging, deposition or distillation and filtration (see, for example EP 0 038 986 A2).

On an industrial scale, polyether polyols are usually produced by addition of alkylene oxides, in particular polypropylene oxide and/or ethylene oxide, to starting compounds with acidic hydrogen atoms (for example water, polyalkylenes or polyamines) in the presence of basic substances, generally alkali metal hydroxides such as KOH or NaOH, as a catalyst. In one of the processing methods which is customary at present, the basic catalyst (for example KOH) is removed from the alkaline polymerizate in a plurality of method steps. First, the alkaline polymerizate is neutralized e.g. with dilute sulfuric acid, after which the majority of water is distilled off with simultaneous crystallization of the inorganic salt (here $K_2SO_4$). The precipitated salt is filtered off, whereupon the residual water is distilled off and the residual amount of salt is removed by filtration.

The disadvantages of these known neutralization methods are, on the one hand, the consumption of neutralization acid and very high energy consumption for distilling the water. On the other hand, it is difficult to filter off the usually very finely divided salt.

The polyether polyol mixture obtained after the polymerization consists of an organic phase, which contains polyether polyol and the by-products created during the reaction (inter alia 1,4-dioxane, 2,5-dimethyl-1,4-dioxane, 2,4-dimethyl-1,3-dioxalane, 2-ethyl-4-methyl-1,3-dioxalane, 2-methyl-2-pentanal, acetaldehyde, acetone, allyl alcohol, allyloxipropanol, DPG allyl ether, ethylbenzene, ethylene, ethylene oxide, methanol, propionaldehyde, propylene oxide and/or toluene). Water is dissolved in this phase, the extent of which depends on the type of polyether polyol, i.e. the molecular weight or C chain length and the proportion and distribution of ethylene oxide and propylene oxide. The aqueous phase contains salt, which may contain ions of the alkali and alkaline-earth metal group, for example Li, Na, K, Be, Mg, Ca, Sr, Ba and creates for example $H_2SO_4$, HCl, $H_3PO_4$, $HNO_3$ or $CO_2$ during the treatment or neutralization with acids. A water-immiscible aromatic or aliphatic solvent (for example toluene or hexane) may furthermore be used in order to improve the phase separation.

In the specific case of producing polycarbonate, copolycarbonate or polyester carbonate according to the so-called phase interface method (cf. phase interface method for polycarbonate production, see Ullmann's Encyclopedia of Industrial Chemistry 2002 Wiley-VCH Verlag), dihydroxyarylalkanes in the form of their alkali metal salts are reacted with phosgene in the heterogeneous presence of inorganic bases such as sodium hydroxide or an inorganic solvent (for example chlorobenzene and/or methylene chloride), in which the polycarbonate product is highly soluble. During the reaction, the aqueous phase is distributed in the organic phase and after the reaction, the organic phase containing polycarbonate is washed with an aqueous liquid and neutralized with acids (for example HCl), so that inter alia electrolytes (for example sodium chloride, sodium carbonate, optionally sodium sulphate) and traces of unreacted raw materials (for example phenol, isooctylphenol, ethyl piperidine and bisphenol) are removed, and the washing liquid is subsequently separated. The aqueous phase is conventionally separated by spray drying, evaporation-extrusion, precipitation of the polycarbonate, centrifuging (see EP 264 885 A2) or by fiber coalescence (see DE 19 510 061 A1).

In general, salts constitute contamination and must be separated from the organic product (for example polycarbonate or polyether polyol).

The object can be achieved by a novel filtration method in which both water and electrolytes (alkalis, acids, salts) are retained, and only the organic phase optionally with residues of physically dissolved water is let through organophilic filters.

Filtration methods are conventionally used for solid-liquid separation, for example to separate particles. They have the disadvantage that they are not capable of separating finely distributed dispersions or emulsions of water and salt in organic solvents (products) from one another. Conventional membrane filtration methods by means of polymer membranes (for example of polyether sulfone, polysulfone, polyamide, cellulose acetate) generally separate the aqueous phase from the organic-aqueous mixture, so that the filtered aqueous phase contains the electrolytes and is generally the desired product, and the organic phase often contains residual electrolytes and must therefore be treated separately or is disposed of. They furthermore have the disadvantage of low chemical stability with respect to organic compounds and a high temperature sensitivity.

Another way of separating the phases from one another is to use membranes which separate water selectively (see Verfahren zur Pervaporation oder Dampfpermeation; see Melin, Rautenbach—Membranverfahren—Springer Verlag 2004). In this case, the aqueous phase penetrates through the membrane and the organic phase is retained. In the case of salt-containing solutions, precipitation of the salts takes place in the region of the separating and support layers of these membranes, so that these membranes are susceptible to clogging. At the same time, these membranes exhibit a low permeation flux.

Feng et al. have furthermore described the use of superhydrophobic coated sieves for separating diesel oil and water. (Feng, L., Zhang, Z., Mai, Z., Ma, Y., Liu, B., Jiang, L. & Zhu, D., A Super-Hydrophobic and Super-Oleophilic Coating Mesh Film for the Separation of Oil and Water. Angewandte Chemie, 116 (2004) 2046). Besides production of the superhydrophobic coated sieves, Feng et al. describe the influence of the sieve mesh width on the hydrophobicity of the sieve. The superhydrophobicity is described with the aid of water drops and diesel oil drops. The separation of diesel oil-water is described as a possible field of use, the liquids being, however, explicitly described as non-emulsified. The work by Feng relates exclusively to the production of the superhydrophobic sieve for separating water and diesel oil. The separation of salt-containing or electrolyte-containing aqueous phases is not described and carried out.

It is therefore an object of the present invention to enable or improve the separation of an electrolyte-free organic phase from an electrolyte-containing (salt-containing) aqueous and organic phase.

SUMMARY OF THE INVENTION

It has now been found that this object can be achieved by the special separation method described below. This is substantially a method of separation via a separating means comprising hydrophobic or hydrophobicized material, which may be formed as a membrane or mesh, by means of which the aqueous phase and electrolytes (salts, alkalis, acids) can be retained while the organic phase permeates through the material (membrane, mesh). Substantial separation of the electrolyte-containing aqueous phase from the organic phase can thereby be achieved.

DETAILED DESCRIPTION

The invention provides a method for separating an organic phase from a mixture of an organic phase comprising an organic solution and an aqueous phase comprising an electrolyte-containing water, characterised in that the mixture to be separated is passed over a hydrophobic porous separating means, in particular an organophilic membrane or a flat textile structure or a perforated plate, in particular a flat textile structure of metal or plastic which either is inherently hydrophobic or which has a hydrophobic coating or hydrophobic surface, at least a part of the organic phase of the mixture permeating through the separating means while the electrolyte-containing aqueous phase is retained fully or to a large part together with the remainder, if any, of the organic phase.

An organophilic (hydrophobic) separating means in the context of the invention comprises a separating means having a surface which has a water contact angle in air of >90° under standard conditions of temperature and pressure.

The separating means is preferably an organophilic membrane of ceramic, metal, polymer, glass or composite materials of ceramic and glass and/or polymer and ceramic, which either has a coating of organophilic material, for example perfluoro polymers (polytetrafluoroethylene (PTFE), polyvinylidene fluoride (PVDF)), hydrophobic polymers (for example polypropylene PP, poly(methylsilsesquioxan) PMSSQ) or a coating formed from reactive materials such as isocyanates, silanes or hybrid copolymers.

The organophilic membrane particularly preferably is formed of ceramic, metal, polymer, glass or corresponding composite materials of ceramic and glass or of polymer and ceramic or metal, which has a sufficient hydrophobicity (or organophilicity) without further modification (e.g. coating).

A particularly preferred method is characterised in that the organophilic membrane is a hydrophobicized ceramic membrane.

In particular, membranes formed from base materials such as $Al_2O_3$, $ZrO_2$, $TiO_2$, SiC (silicon carbide) or combinations of these compounds are used as ceramic membranes.

The organophilic ceramic membrane has in particular a pore width of from 0.05 μm to 10 μm, particularly preferably from 0.1 μm to 5 μm.

Electrolytes in the context of the invention are salts, alkalis or acids, in particular inorganic compounds, dissolved in water.

A particularly preferred method/separating means is characterised in that the hydrophobic porous membrane is an organophilic polymer membrane. In particular, membranes formed of polymers selected from the group consisting of (PP polypropylene), (PVDF polyvinylidene fluoride), (PTFE polytetrafluoroethylene), silicones and combinations of such polymers are used as organophilic polymer membranes.

The organophilic polymer membrane has pores with in particular a pore width of from 0.05 μm to 10 μm, particularly preferably from 0.1 μm to 5 μm.

An alternative preferred method is characterised in that a woven metal mesh with a hydrophobic coating is used as the hydrophobic porous separating means, the metal mesh preferably having a mesh width <500 μm, more preferably <50 μm, most preferably <5 μm.

A suitable organophilic material particularly preferred for a hydrophobic coating is selected from a list of the following materials but not in principle restricted thereto: PTFE (for example Teflon® AF, available from DuPont), PTFE dispersion, isocyanates, organic and/or fluoro polymers or latex, hybrid copolymers, fatty acids, silanes, lacquers, silicones, silicone oils or polysilsesquioxans, or organic and/or fluoro deposits applied from a plasma process, or a mixture of different aforementioned coating agents. The hybrid copolymers are in particular diblock copolymers containing one hydrophobic polymer block which binds readily to the metal mesh and one hydrophobic polymer block which does not bind to the metal mesh, wherein a preferred variant of the binding block consists of a polysilsesquioxan, and particularly preferably poly(methylsilsesquioxan) or poly(stearylsilsesquioxan) and a particularly preferred variant of the non-binding hydrophobic polymer block can be selected from, but is not limited to, the group comprising polystyrene, polymethyl acrylate, polyethyl hexyl acrylate, polymethyl methacrylate and polydecyl methacrylate.

A particularly preferred method is characterised in that a hydrophobic flat textile structure, in particular a woven, knitted fabric, felt of hydrophobic plastic (in particular polypropylene, PTFE or PVDF) without further modification is used as the hydrophobic porous separating means. The hydrophobic flat textile structure preferably has a pore/mesh width <500 μm, more preferably <50 μm, most preferably <5 μm.

In a more particularly preferred method, the hydrophobic coating is produced by applying a smooth hydrophobic coating onto a previously roughened surface of the separating means.

The method is preferably employed when the mixture to be separated is an emulsion or dispersion comprised of water, electrolyte and organics, in particular electrolytes of the alkali and/or alkaline-earth metals, and organics of polymers, aromatics and/or aliphatics.

The method is particularly preferably employed when the mixture to be separated is an emulsion or dispersion of an organic phase comprising polycarbonate dissolved in organic solvent, and an aqueous phase comprising water and optionally including salts of the alkali and alkaline-earth metals, in particular sodium, potassium, magnesium and/or calcium.

The method is also preferably employed when the mixture to be separated is an organic phase comprising a mixture of a polyol, optionally in a solvent such as an aromatic or aliphatic hydrocarbons for example toluene or hexane, and an aqeious phase comprising water and a salt of the alkali and alkaline-earth metals, such as sodium, potassium, magnesium or calcium.

The hydrophobic separating means in the method according to the invention is characterized by a high separation rate of salt and water from the organic mixture, together with a high permeation flux and a high stability with respect to organic solvents.

Salts contained in the mixture to be separated are mostly retained together with the aqueous phase and can then readily be removed.

A hydrophobicized mesh particularly preferably is one formed of a shape- and pressure-stable stainless steel, particularly preferably of a shape- and pressure-stable austenitic stainless steels (1.4404, 1.4571). The mesh is preferably to be employed with a mesh width <500 µm, more preferably with a mesh width <100 µm, particularly preferably with a mesh width 20 µm and most preferably with a mesh width <5 µm.

The coating of the mesh preferably is formed of a hydrophobic material, more preferably of nonpolar polymers, hybrid copolymers, polysilsesquioxans or silanes, particularly preferably of polysilsesquioxan block polymers or polytetrafluoroethylene. The hydrophobic material may in this case be applied by spraying, solution wetting, sublimation or other suitable methods.

In the simplest case, the mesh is modified by applying a solution of a dissolved hydrophobic material with subsequent evaporation of the solvent, preferably by evaporating an applied polymer solution, preferably a polysilsesquioxan block copolymer solution, polytetrafluoroethylene solution or i-polypropylene solution (Erbil, H. Y., Demirel, A. L., Avcinodot, Y. & Mert, O., Transformation of a Simple Plastic into a Superhydrophobic Surface. *Science*, 299, No 5611, (2003) 1377-80), and particularly preferably a solution of poly(methylsilsesquioxan) block poly(methylmethacrylat).

As an alternative, the mesh may also be modified by the covalent bonding of hydrophobic silanes (Nakajima, A., Abe, K., Hashimoto, K. & Watanabe, T., Preparation of hard superhydrophobic films with visible light transmission. *Thin Solid Films*, 376, No 1-2, (2000) 140-3; Nakajima, A., Fujishima A., Hashimoto, K. & Watanabe, T., Preparation of Transparent Superhydrophobic Boehmite and Silica Films by Sublimation of Aluminum Acetylacetonate, *Advanced Materials*, 11, No 16, (1999) 1365); Bico, J., Marzolin, C. & Quere, D., Pearl drops, *Europhys Lett*, 47, No 2, (1999) 220).

Another way of modifying the mesh is to treat the metal mesh by spraying on a polymer dispersion, for example a polytetrafluoroethylene dispersion in water, and subsequent sintering at a temperature of about 320° C., or a poly(methylsilsesquioxan) block poly(methylmethacrylate) solution in THF and subsequent sintering at a temperature of about 130° C.

The hydrophobicity of the layer may be further increased by increasing the roughness of the surface, preferably by sandblasting or etching the metal mesh prior to coating, by adding nanoparticles into the coating, or by subsequent plasma treatment of the coating (Morra, M., Occhiello, E. & Garbassi F., Contact angle hysteresis in oxygen plasma treated poly(tetrafluoroethylene) Langmuir, 5, No 3, (1989) 872).

After modification, a water contact angle (measured against air)>90°, preferably >120°, particularly preferably >140° is obtained on the layer.

Another way of achieving the object is to use hydrophobicized ceramic membranes. In this case, the organic phase likewise passes through the membrane and the electrolyte-containing aqueous phase is retained. The electrolytes/salts remain in the water, so that no clogging of this membrane by salts takes place as occurs in the case of hydrophilic water-selective membranes. The production of hydrophobicized ceramic membranes is described, for example, in DE 10 308 110 A1 (U.S. 2006/0237361 A1) using fluorosilanes. At the same time, it is feasible to produce hydrophobic membranes of $SiO_2$ or Vycor glass. The hydrophobicized ceramic membranes used may have a pore size of from 0.05 to 10 µm, particularly preferably between 0.1 and 5 µm.

Another way of achieving the object is to use hydrophobic polymer membranes of PP, PVDF or PTFE which have sufficient chemical stability with respect to the organic phases respectively employed. In this case, the substantially electrolyte-free organic phase likewise passes through the membrane and the electrolyte-containing aqueous phase is retained. Membranes of polypropylene (PP) with a pore size of from 0.05 to 3 µm, particularly preferably from 0.1 to 1 µm, are particularly suitable.

By using the method according to the invention, for example, a substantially electrolyte-free organic polyether polyol could be separated from a polyether polyol solution containing a dispersed aqueous phase of electrolyte, i.e. a salt, and water in a single separation stage as far as physical solubility of the water in the polyol being used. The salt-containing aqueous phase, as the disperse phase, can thus be almost entirely separated. At the same time, the salt ($K_2SO_4$) can be retained up to 99.9%. The salt retention could even be observed when a polyether almost entirely miscible with water was used. In this case, the phase remaining in the retentate was enriched with salt.

By using the method according to the invention, for example, a substantially salt-free organic polycarbonate solution could also be separated from a polycarbonate solution containing an aqueous phase of electrolyte and water, in a single separation stage, to a water content reaching 0.1% or as far as physical solubility in the separated polycarbonate solution. At the same time, the salt (NaCl) could be retained at up to 99.9%, expressed in terms of the initial value of the polycarbonate solution. The electrolyte-containing aqueous phase, as the disperse phase, was thus almost entirely separated from the organic phase.

BRIEF DISCUSSION OF THE DRAWINGS

The invention will be explained in more detail below by way of example with the aid of FIG. 1, in which:
1 is a stirring tank/vessel
2 is a circulating pump
3 is a membrane module for the sieve/membrane
4 is a hydrophobic sieve/membrane
5 is a valve
6 is the organic phase (permeate)
7 is the aqueous phase (retentate)

EXAMPLES

In order to carry out the method according to the invention, a crossflow filtration cell 3 with a hydrophobic separating means 4 is used. The solution to be separated is placed in the stirring tank 1 and pumped in a circuit by a pump 2 through the separating means (membrane/sieve) 4 at a predetermined crossflow rate. An appropriate transmembrane pressure difference (TMP=$(p_{feed}+p_{retentate})/2-p_{permeate}$) can be set using a valve 5 so that the organic solution, which has a lower water and salt concentration in the permeate 6 than in the retentate 7, permeates through the separating means (membrane/sieve) (i.e. permeate). The electrolyte/salt-containing aqueous and organic phase depleted of organics (retentate 7) is returned into the stirring tank 1. A Karl-Fischer titration is carried out for analytical determination of the water equivalent. The respective electrolyte (salt) concentration is determined by titrating the entire base content or by atomic absorption spectroscopy (AAS). The detection limit for Na is 15 ppb (µg/kg).

Example 1

Production of a Hydrophobicized Sieve

An austenitic steel with the designation 1.4404 is used as the basis for production of a superhydrophobic sieve. The absolute filter unit is 5 μm (DTW 4). The metal sieve is cleaned in a 1:1 mixture consisting of ethanol and n-hexane. The surface is subsequently etched with a mixture of $H_2O$, $H_2O_2$ and ammoniacal water at 80° C. After washing with water, coating is carried out with a 5% strength Teflon® dispersion 30-N. In order to dry the PTFE dispersion, the sieve is sintered at 320° C. for 30 minutes. The water contact angle of a mesh coated in this way is 140°±5'. This was found by measuring the so-called static contact angle of an approximately 10 μm large drop of distilled water on the mesh at room temperature.

Example 2

As described in the general experimental method, a hydrophobic mesh produced according to Example 1 (sieve 06 DTW mesh width 4 to 5 μm, hydrophobicized with 5% of Teflon® N 30) is used in the test apparatus described above. The filtration surface is 0.0044 m². A polyether polyol solution is employed (trimethylolpropane started polyether with a trifunctionality and an OH number of 45, side chains with 16% ethylene oxide units and predominantly secondary OH groups). Table 1 shows the result of the phase separation.

TABLE 1

| Tank [° C.] | Crossflow [m/s] | TMP [bar] | Permeate flux [kg/m²hbar] | Feed [% $H_2O$] | Permeate [% $H_2O$] |
|---|---|---|---|---|---|
| 78.7 | 1.5 | 0.06 | 403.4 | 7.8 | 5.6 |
| 78.7 | 1.5 | 0.06 | 375.0 | 8.1 | 5.7 |
| 79.0 | 1.5 | 0.07 | 761.5 | 8.1 | 5.6 |
| 78.9 | 1.5 | 0.18 | 542.9 | 8.1 | 5.6 |
| 79.0 | 1.5 | 0.22 | 458.7 | 8.2 | 5.6 |
| 79.0 | 1.5 | 0.36 | 265.2 | 8.1 | 5.6 |
| 79.3 | 1.5 | 0.36 | 238.9 | 8.2 | 5.9 |
| 78.7 | 1.5 | 0.40 | 211.9 | 8.2 | 5.9 |

Example 3

As described in the general experimental method, a hydrophobic mesh produced according to Example 1 (sieve 06 DTW mesh width 4 to 5 μm, hydrophobicized with 5% of Teflon N 30) with a PTFE sealing edge molded in, is used in the test apparatus described above. The filtration surface is 0.0044 m². The experiment was conducted similarly as Example 2. A polyether polyol solution is employed (product as in Example 2). Table 2 shows the result of the phase separation.

TABLE 2

| Tank [° C.] | Crossflow [m/s] | TMP [bar] | Permeate flux [kg/m²hbar] | Feed [ppm KOH] | Permeate [ppm KOH] | Feed [% $H_2O$] | Permeate [% $H_2O$] |
|---|---|---|---|---|---|---|---|
| 114.3 | 1.5 | 0.3 | 1246 | 1826 | 0.1 | 4.0 | 4.0 |
| 114.9 | 1.5 | 0.5 | 766 | 1859 | 5.8 | 4.0 | 3.9 |
| 115.5 | 1.5 | 1.0 | 464 | 2194 | 4.2 | 4.1 | 3.8 |

Example 4

The method is similar to Example 2, but using a ceramic organophilic membrane. The membrane, a so-called monochannel tube with a tubular channel, having an internal diameter of 6 mm and a length of 250 mm and an active inner filtration surface of 0.005 m², consists of $Al_2O_3$ and was silanized according to the description in patent specification DE 10 308 110 A1 (U.S. 2006/0237361 A1). The pore diameter of the membrane is 3 μm.

By continuously pumping the feed solution (product as in Example 2) over the inside of the membrane being used, a clear polyether permeate could be drawn off, the water concentration being in the range of physical solubility. An increase of the water concentration in the feed could correspondingly be achieved, which corresponds to concentrating the aqueous phase in the circuit.

Table 3 shows the phase separation of the polyether by means of a hydrophobic ceramic membrane with a pore size of 3 μm.

TABLE 3

| Tank [° C.] | Crossflow [m/s] | TMP [bar] | Permeate flux [kg/m²hbar] | Feed [% $H_2O$] | Permeate [% $H_2O$] |
|---|---|---|---|---|---|
| 77.0 | 1.0 | 0.65 | 47.1 | 8.5 | 5.9 |
| 81.0 | 2.0 | 1.36 | 56.3 | 8.3 | 4.8 |
| 79.6 | 3.0 | 2.11 | 64.5 | 8.4 | 5.2 |
| 80.1 | 3.0 | 2.15 | 63.3 | 8.6 | 4.7 |
| 80.1 | 3.0 | 2.11 | 56.0 | 8.8 | 5.2 |
| 80.1 | 3.0 | 2.11 | 49.4 | 9.1 | 4.7 |
| 80.1 | 3.0 | 2.1 | 47.1 | 10.0 | 4.6 |
| 80.1 | 3.0 | 2.13 | 45.7 | 11.1 | 4.5 |
| 80.1 | 3.0 | 2.21 | 41.5 | 11.3 | 4.9 |

Example 5

A polycarbonate solution (PC molecular weight $M_w$ approximately 18,000 to 19,000 g/mol), coming from a washing stage in the interface method for producing polycarbonate, consisting of polycarbonate, monochlorobenzene, methylene chloride and sodium salts (NaCl) as well as minor amounts of water, neutralized with hydrochloric acid (HCl), was used in the system described above. The sodium content in the feed solution was 4.3 ppm (4300 ppb) at the start of the experiment. The polycarbonate phase was turbidified by the aqueous emulsion. By using the method according to the invention, it was possible to separate a salt-free organic solution by means of an organophilic ceramic membrane. The membrane, a so-called multichannel tube with 7 tubular channels, having an internal channel diameter of 6 mm and a length of 250 mm and an active inner filtration surface of 0.03 m², consists of $Al_2O_3$ and was silanized according to the description in patent specification DE 10 308 110 A1 (U.S. 2006/0237361 A1). The pore diameter of the membrane is 1 μm. The results of the experiment are presented in Table 4, and clearly show the reduction of the sodium content of the polycarbonate solution. All permeate samples are clear and have no turbidity to the naked eye.

TABLE 4

| Tank [° C.] | Crossflow [m/s] | TMP [bar] | Permeate flux [kg/m²hbar] | Permeate [ppb Na] |
|---|---|---|---|---|
| 36.8 | 1.2 | 2.06 | 55.8 | 20 |
| 37.5 | 1.1 | 2.10 | 45.9 | <15 |
| 35.9 | 1.1 | 2.15 | 28.6 | <15 |

Example 6

A polycarbonate solution coming from a washing stage in the interface method, consisting of polycarbonate, monochlorobenzene, methylene chloride and sodium salts (NaCl) as well as minor amounts of water, neutralized with hydrochloric acid (HCl), was used in the system described above (FIG. 1). The sodium content in the feed solution was 0.8 ppm (800 ppb) at the start of the experiment. The water content was determined as 0.22 wt. % at the start of the experiment. The polycarbonate phase was turbidified by the aqueous emulsion. By using the method according to the invention, it was possible to separate a salt-free organic solution by means of an organophilic ceramic membrane consisting of silanized $Al_2O_3$, as described in Example 3, but with a pore size of 0.8 µm. The results of the experiment are presented in Table 5, and clearly show the reduction of the sodium content and water content of the polycarbonate solution. All permeate samples are clear and have no turbidity to the naked eye.

TABLE 5

| Tank [° C.] | Crossflow [m/s] | TMP [bar] | Permeate flux [kg/m²hbar] | Permeate [ppb Na] | Permeate [% H₂O] |
|---|---|---|---|---|---|
| 27.9 | 0.8 | 2.08 | 36.9 | 20 | 0.09 |
| 28.6 | 0.7 | 2.02 | 31.0 | <15 | 0.08 |
| 27.4 | 0.7 | 2.08 | 14.2 | <15 | 0.10 |

Example 7

A still alkaline polycarbonate solution i.e. containing electrolyte (not neutralized) coming from a washing stage in the interface method, consisting of polycarbonate, monochlorobenzene, methylene chloride and sodium hydroxide as well as minor amounts of water, was used in the system described above. The sodium content in the feed solution was 2.9 ppm (2900 ppb) at the start of the experiment. The water content was determined as 5.4 wt. % at the start of the experiment. The polycarbonate phase was turbidified by the aqueous emulsion. By using the method according to the invention, it was possible to separate an electrolyte-free organic solution by means of an organophilic PP polymer membrane. The PP membrane used is tubular with an internal diameter of 5.5 mm and an external diameter of 8.5 mm, a length of 250 mm and an active inner filtration surface of 0.004 m². The pore diameter of the membrane is 0.2 µm. The results of the experiment are presented in Table 6, and clearly show the reduction of the sodium content and water content of the separated polycarbonate solution. All permeate samples are clear and have no turbidity to the naked eye.

TABLE 6

| Tank [° C.] | Crossflow [m/s] | TMP [bar] | Permeate flux [kg/m²hbar] | Permeate [ppb Na] | Permeate [% H₂O] |
|---|---|---|---|---|---|
| 33.3 | 3.14 | 0.70 | 64.0 | <15 | 0.09 |
| 33.2 | 3.14 | 0.67 | 23.3 | <15 | 0.1 |
| 33.1 | 3.14 | 1.18 | 8.6 | 20 | 0.1 |
| 33.1 | 3.14 | 1.18 | 3.8 | <15 | 0.1 |

Example 8

THF was distilled over sodium/benzophenone under nitrogen and all of the monomers employed were recondensed under reduced pressure prior to polymerization. CuBr was stirred for 24 h with acetic acid, filtered off, washed with methanol and dried in vacuo.

Synthesis of pent-4-enyl 2-bromoisobutyrate (1). 160 mmol (13.9 g) penten-4-ol and 50 ml chloroform were introduced into a flask and cooled to 0° C. 160 mmol (36.8 g) bromoisobutyryl bromide in 20 ml chloroform were introduced slowly with cooling and the resulting solution was stirred for 4 h at room temperature. The reaction solution was washed three times with water, dried over $MgSO_4$ and then concentrated by evaporation. The product was distilled in a high vacuum. Boiling point at $3.3 \times 10^2$ mbar: 50° C. Yield: 34.79 g (148 mmol; 92.5%)

$^1$H NMR ($CDCl_3$); (ppm)=5.74 (m, 1H); 4.96 (m, 2H); 4.12 (t, 3J=6.6 Hz, 2H); 2.10 (m, 2H); 1.87 (s, 6H); 1.72 (quin, 3J=6.3 Hz, 2H)

$^{13}$C NMR ($CDCl_3$); (ppm)=171.34; 137.05; 115.35; 65.05; 55.66; 30.58; 29.73; 27.37. FD mass spectrum: 234.0 (27.8%); 235.0 (100%)

EA (%): calculated: C=45.98; H=6.43; found: C=45.87; H=6.43.

Synthesis of the PMSSQ macroinitiator 5-(trichlosilanyl)-pentyl 2-bromoisobutyrate (2). Methyltrimethoxysilane (MTMS) and (1) in a molar ratio of 20:1 were dissolved in 20 ml THF and 1000 mol % water and 3 mol % HCl were added. The solution was then stirred for 3 h at 0° C., extracted with diethyl ether and the ether extract was washed with water and dried over $MgSO_4$. The solvent was evaporated off and the product dried in a high vacuum.

$^1$H NMR ($CDCl_3$); (ppm)=5.55 (br); 4.14 (br, 2H); 3.44 (s); 1.91 (br, 6H); 1.77 (br, 2H); 1.60 (br, 2H); 1.42 (br, 2H); 0.63 (br, 2H); 0.13 (br)

$^{29}$Si solid state NMR; (ppm)=−48.26 (T1); −57.23 (T2); −65.87 (T3)

Synthesis of poly(methylsilsesquioxan) block poly(methylmethacrylate) (3) by means of atom transfer radical polymerization. The macroinitiator (2) (0.5 g), CuBr and 2,2'-bipyridine in a ratio of 1:1:2, and methyl methacrylat (2 g) were degassed three times in 4 ml dioxan. The solution was stirred for 8 h at 55° C. and the hybrid copolymer was precipitated with n-heptane and then reprecipitated twice from THF in n-heptane and dried in a high vacuum.

$^1$H NMR ($CDCl_3$); (ppm)=4.92 (br); 3.57 (br); 1.72 (br); 1.03 (br); 0.15 (br).

Coating: A mesh in the form of a metal mesh of type DTW4 from Haver and Böcker of a diameter of about 89 mm of austenitic steel labelled 1.4404 is used as the basic separating means, the absolute filtering unit of which (the nominal pore size) is 5 µm. About 10 ml of a solution of the hybrid copolymer PMSSQ-b-PMMA (3) in THF with a concentration of 2.5 mg/ml is introduced into a Petri dish and the sieve is immersed horizontally into the solution for 30 mins, then also washed with THF for about 5 minutes in the Petri dish and then heated for 1 hour at 130° C. in a drying cabinet as contactlessly as possible. The water contact angle of a sieve coated in this manner is 93°. The advancing contact angle of an approximately 10 µl large drop of distilled water on the sieve is measured at room temperature.

Example 9

This is carried out analogously to Example 2 but using the hydrophobicized mesh from Example 8. A polyether polyol solution is used (the same product as in Example 2). Table 7 shows the results of phase separation.

TABLE 7

| Vessel [° C.] | Crossflow [m/s] | TMP [bar] | Permeate flux [kg/m²h] | Feed [ppm KOH] | Permeate [ppm KOH] | Feed [% H₂O] | Permeate [% H₂O] |
|---|---|---|---|---|---|---|---|
| 88.2 | 0.9 | 0.02 | 61.9 | 2051 | 27 | 8.6 | 4.1 |
| 89.1 | 0.9 | 0.04 | 50.2 | n.d.* | 28 | n.d. | 4.2 |
| 89.5 | 0.91 | 0.02 | 85.2 | n.d. | 27 | n.d. | 3.9 |

*not determined

The invention claimed is:

1. Method for separating an organic phase from a mixture of an organic phase comprising a polycarbonate solution and an aqueous phase comprising an electrolyte-containing water, wherein the mixture to be separated is passed over a hydrophobic porous separating means, said hydrophobic porous separating means being an organophilic ceramic membrane consisting of $Al_2O_3$ coated with a silane, said silane coating being produced by applying a smooth coating of the silane onto a previously roughened surface of the ceramic membrane, at least a part of the organic phase of the mixture permeating through the separating means while the electrolyte-containing aqueous phase is at least partially retained together with the remainder, if any, of the organic phase, said at least part of the organic phase permeating through the separating means having a water content of 0.1% by weight or less.

2. Method according to claim 1, wherein the ceramic membrane has a pore width of from 0.05 μm to 10 μm.

3. Method according to claim 2, wherein said pore width is from 0.1 μm to 5 μm.

* * * * *